(12) United States Patent
Dowle et al.

(10) Patent No.: US 6,228,853 B1
(45) Date of Patent: May 8, 2001

(54) PYRROLOPYRROLONE DERIVATIVES AS INHIBITORS OF NEUTROPHIL ELASTASE

(75) Inventors: Michael Dennis Dowle; Harry Finch; Lee Andrew Harrison; Graham George Adam Inglis; Martin Redpath Johnson; Simon John Fawcett MacDonald, all of Stevenage (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/508,326

(22) PCT Filed: Sep. 7, 1998

(86) PCT No.: PCT/EP98/05604

§ 371 Date: Jun. 2, 2000

§ 102(e) Date: Jun. 2, 2000

(87) PCT Pub. No.: WO99/12931

PCT Pub. Date: Mar. 18, 1999

(30) Foreign Application Priority Data

Sep. 9, 1997 (GB) .................................................. 9719187

(51) Int. Cl.$^7$ ......................... C07D 487/02; A61K 31/40
(52) U.S. Cl. .................. 514/210.18; 514/322; 514/414; 546/199; 548/453
(58) Field of Search ............................ 548/453; 546/199; 514/210.18, 322, 414

(56) References Cited

U.S. PATENT DOCUMENTS

| | | |
|---|---|---|
| 3,983,245 | 9/1976 | Ladd et al. . |
| 6,057,457 * | 5/2000 | Dowle et al. ........................ 548/550 |

FOREIGN PATENT DOCUMENTS

| | | |
|---|---|---|
| 0201957A | 11/1996 | (EP) . |
| WO9324519A | 12/1993 | (WO) . |
| WO9521855A | 8/1995 | (WO) . |
| WO9725309A | 7/1997 | (WO) . |
| WO9736903A | 10/1997 | (WO) . |

OTHER PUBLICATIONS

D.L. Lee et al., "Alpha–Methylenelactam Rearrangement", vol. 39, No. 7, pp. 893–902, Easton, US, 1974.

* cited by examiner

Primary Examiner—Deborah C. Lambkin
Assistant Examiner—Sonya N. Wright
(74) Attorney, Agent, or Firm—James P. Riek

(57) ABSTRACT

According to the invention are provided compounds of formula (I) (relative stereochemistry indicated) wherein $R^1$, $R^2$ and $R^3$ are as defined in the specification. Compounds of formula (I) are useful inter alia in the treatment of inflammatory diseases of the respiratory tract.

21 Claims, No Drawings

PYRROLOPYRROLONE DERIVATIVES AS INHIBITORS OF NEUTROPHIL ELASTASE

This application is filed pursuant to 35 U.S.C. §371 as a United States National Phase Application of International Application No. PCT/EP98/05604 filed Sep. 7, 1998, which claims priority from GB9719187.8 filed Sep. 9, 1997.

The present invention relates to therapeutically active bicyclic compounds, processes for their manufacture, pharmaceutical formulations containing them and their use in chemotherapy. In particular, we have found a group of novel bicyclic compounds which are effective in treating inflammatory diseases.

Inflammation is a primary response to tissue injury or microbial invasion and is characterised by circulating leukocytes binding to and extravasation through vascular endothelium. Circulating leukocytes include neutrophils, eosinophils, basophils, monocytes and lymphocytes. Different forms of inflammation involve different types of infiltrating leukocytes.

The inflammatory process can be triggered in a number of ways, including by infection, tissue damage and autoimmune reactions. As part of the inflammatory process, neutrophils move from the bloodstream into the tissue at the site of tissue lesion. The neutrophils contain large numbers of different intracellular granules and when activated at the site of inflammation the contents of these granules are secreted into the tissue. The different granules contain a variety of enzymes and other proteins, many of which have antibacterial properties.

One of the enzymes found in the azurophilic granules is neutrophil elastase. Neutrophil elastase has a wide spectrum of activities in the body. For example, within the lung the enzyme increases mucus production and changes the cellular composition of the epithelium The enzyme also causes vascular permeability changes within the microcirculation of many tissues and it is a potent destructive agent against a number of connective tissue components.

Although there are within the body endogenous inhibitors of elastase, including the anti-trypsin and the leukocyte protease inhibitor, elastase activity has been implicated in the pathogenesis of a number of disease states including inflammatory diseases of the airways, the joints and the skin. The enzyme is also responsible for some or most of the symptoms of acute respiratory distress syndrome (ARDS) and other acute inflammatory states brought about by trauma and/or sepsis.

We have now found a group of novel compounds which inhibit neutrophil elastase. These compounds are therefore of potential therapeutic benefit in the treatment and amelioration of symptoms of diseases where elastase activity is implicated.

Thus, according to one aspect of this invention, we provide a compound of the formula (I)

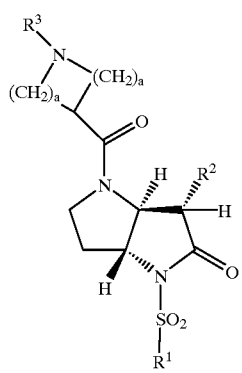

(I)

(relative stereochemistry indicated)
wherein:
$R^1$ represents $C_{1-6}$alkyl;
$R^2$ represents $C_{2-4}$alkyl or $C_{2-4}$alkenyl;
a represents 1 or 2;
$R^3$ represents $C_{1-8}$alkyl or $(CH_2)_n Ar$;
n represents 1 or 2;
Ar represents optionally substituted phenyl;
and salts and solvates thereof (hereinafter "compounds of the invention").

Formula (I) shows the relative stereochemistry of the chiral centres. The invention embraces compounds of the invention in racemic form as well as in a form in which one enantiomer predominates or is present exclusively. Generally, we prefer to provide a compound of formula (I) in enantiomerically pure form, most particularly the enantiomer having the absolute stereochemistry illustrated in formula (I).

The present invention also covers the physiologically acceptable salts of the compounds of formula (I). Suitable physiologically acceptable salts of the compounds of formula (I) include inorganic and organic acid salts such as hydrochloride and tartrate.

Examples of groups by with the phenyl of Ar may be substituted include halogen, $C_{1-4}$alkyl, $C_{1-4}$alkoxy, nitro, hydroxy, amine (optionally substituted by one or two $C_{1-4}$alkyl groups), $CF_3$, COOH, $COOC_{1-4}$alkyl and $CONH_2$ (optionally substituted by one or two $C_{1-4}$alkyl groups).

When used herein "alkyl" includes branched as well as straight chain alkyl and may also include cycloalkyl when 3 or more carbon atoms are present.

Suitable $R^1$ alkyl groups include methyl, ethyl and propyl.
Suitable $R^3$ $C_{1-8}$ alkyl groups include n-butyl, cyclopropyl and t-butyl.

We prefer $R^1$ to represent methyl or ethyl, especially methyl.

We prefer $R^2$ to represent isopropyl or propyl, especially isopropyl.

We prefer a to represent 1.

We prefer $R^3$ to represent $C_{1-8}$ alkyl or $CH_2Ar$. Preferred Ar includes phenyl and phenyl substituted by one or more halogen groups.

The potential for compounds of the invention to inhibit neutrophil elastase activity may be demonstrated, for example, using the following in vitro and in vivo assays:

In vitro assays of human neutrophil elastase
Assay contents:
50 mM Tris/HCl (pH 8.6)
150 mM NaCl
11.8 nM purified human neutrophil elastase
Suitable concentrations of compound under test diluted with water from a 10 mM stock solution in dimethylsulphoxide. Values above are final concentrations after the addition of substrate solution (see below).

The mixture above is incubated for fifteen minutes at 30° C. at which time the remaining elastase activity is measured for 10 minutes in a BioTek 340i plate-reader, after the addition of 0.6 mM MeO-succinyl-alanyl-alanyl-prolyl-valyl-p-nitroanilide. The rate of increase in absorbance at 405 nm is proportional to elastase activity. Enzyme activity is plotted against concentration of inhibitor and an $IC_{50}$ determined using curve fitting software.

In vivo activity of inhibitors of human neutrophil elastase:
An oral in vivo model using IL-8 induced lung infiltrates for the assessment of intracellular elastase inhibition Adult hamsters (100–150 g) are randomised into groups (n=4) and fasted overnight. Under gaseous anaesthetic (3% isofluorane) animals are dosed orally with 1 mL/100 g water as vehicle or containing predissolved compounds. Either at the same time, or subsequently under anaesthetic, animals are dosed intratracheally with 1 ug recombinant human IL-8 in 100 uL sterile saline. Six hours after IL-8 dosing animals are sacrificed using intraperitoneal pentobarbitone. The lungs are lavaged with 2×2.5 mL sterile saline and femurs are removed by dissection.

Intracellular elastase is prepared from neutrophils collected by lavage and from femoral bone marrow. This is achieved by sonication of the neutrophils and centrifugation to yield intracellular granules. These are disrupted by freeze/thawing and sonication. Elastase and myeloperoxidase assays are then performed on these samples to assess the efficacy of the compounds and to normalise for neutrophil recovery.

Human whole blood elastase inhibition assay

Triplicate aliquots of fresh, heparinised human whole blood (200 μl) are added to appropriately diluted samples (10 μl) of compounds under test. Control samples (6 replicates) contain water in place of compound. Samples are mixed thoroughly by pipette, and are then incubated for 30 minutes at 37° C. Cold red cell lysis buffer (750 μl of 155 mM ammonium chloride, 0.12 mM EDTA, 10 mM potassium bicarbonate, pH 7.4) is then added. Tubes are capped, inverted several times, and maintained at 4° C. for 15 minutes, inverting every 5 minutes. After centrifugation at 250 g for 10 minutes, at 4° C., the resulting pelleted cells are washed. The wash is with saline (300 μl), followed by centrifugation at 100 g for 10 minutes at 4° C. Pellets are washed twice more, before resuspension of the final cell pellet in buffer (200 μl of 100 mM Tris, 300 mM NaCl, 1% (w/v) HTAB, pH 8.6). Samples are stored at −20° C. After freeze-thawing of the samples four times, elastase activity is determined by a calorimetric assay in 50 mM Tris, 150 mM NaCl, 0.6 mM MeO-Succ-Ala-Ala-Ala-Pro-Val-pNA at pH 8.6, measuring the rate of increase in absorbance at 405 nm.

Accordingly, the compounds of the invention are of potential therapeutic benefit in the treatment and amelioration of symptoms of diseases where elastase activity is implicated. Such diseases particularly include bronchitis, including chronic bronchitis. Also any chronic obstructive pulmonary disease (COPD).

Examples of disease states in which the compounds of the invention have potentially beneficial effects include inflammatory diseases of the respiratory tract such as bronchitis (including chronic bronchitis), bronchiectasis, asthma and hyper-reactivity states of the lung, acute respiratory distress syndrome and septic shock, inflammatory or destructive conditions of the lung such as emphysema and cystic fibrosis and inflammatory or destructive conditions of external tissue such as skin diseases (e.g. lupus and psoriasis) and periodontal disease including gingivitis.

Further examples of disease states and conditions in which compounds of the invention have potentially beneficial effects include wound healing and treatment of burns, cardiovascular diseases such as myocardial infarction and stroke, peripheral vascular disease including intermittent claudication, atherosclerosis, reperfusion injury, cardiovascular changes occurring during cardiopulmonary bypass surgery and septicemia.

Compounds of the invention may also be useful in the treatment of connective tissue disorders such as rheumatoid arthritis, osteoarthritis and spondylitis and inflammatory conditions of the kidney such as glomerulonephritis.

They may also be useful in the treatment of certain leukemias including acute myelogenous leukemia, acute myelomonocytic leukemia and the chronic monocytic leukemias and in prevention or inhibition of metastasis of solid tumours e.g. lung, breast, prostate and stomach cancers and melanomas.

A particular aspect of the present invention is the use of compounds of formula (I) in the treatment of chronic bronchitis. Chronic bronchitis is a condition which results from the exposure of the airway surface to noxious chemicals or agents or is secondary to another disease. The symptoms of the condition are caused by the excessive secretion of mucus onto the surface of the airways. This excess mucus cannot be cleared effectively and the result is reduced gas exchange within the lungs resulting in laboured breathing and hypoxemia, recurrent microbial infections and persistent cough associated with the expectoration of mucoid material. The proposed mechanism for the excessive secretion of mucus involves the recruitment of neutrophils into the airways following the exposure of the epithelium to irritant materials; the neutrophils secrete elastase onto the surface of the airways and the enzyme brings about both an increase in the amount of mucus secreted onto the airway surfaces and a dramatic change in the cellular composition of the airway epithelium. Inhibition of elastase activity by the administration of compounds of this invention is therefore an approach to the treatment of chronic bronchitis. Reduced lung function in COPD (eg in chronic bronchitics with airflow obstruction) is also due to elastase mediated lung damage leading to airway narrowing and inflammation. Thus an elastase inhibitor will improve lung function.

As indicated above, compounds of the invention are useful in human or veterinary medicine, in particular as inhibitors of the enzyme neutrophil elastase.

Thus, there is provided as a further aspect of the present invention a compound of formula (I) or a physiologically acceptable salt or solvate thereof for use in human or veterinary medicine, particularly in the treatment of conditions where elastase activity is implicated such as chronic bronchitis.

It will be appreciated that references herein to treatment extend to prophylaxis as well as the treatment of established conditions.

According to another aspect of the invention, there is provided the use of a compound of formula (I) or a physiologically acceptable salt or solvate thereof for the manufacture of a medicament for the treatment of conditions where elastase activity is implicated, particularly in chronic bronchitis.

In a further or alternative aspect there is provided a method for the treatment of a human or animal subject with a condition caused or mediated by elastase activity which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in therapy, comprising a compound of formula (I) or a physiologically acceptable salt or solvate thereof in admixture with one or more physiologically acceptable diluents or carriers.

There is also provided according to the invention a process for preparation of such a pharmaceutical composition which comprises mixing the ingredients.

The compounds according to the invention may, for example, be formulated for oral, buccal, parenteral, topical or rectal administration.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, microcrystalline cellulose, sugar, maize- starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p- hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or toxicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insufflator or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-faqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetrafluoroethane, 1,1,1,2,3,3,3-heptafluoropropane, 1,1,1,2-tetrafluorethane, carbon dioxide or other suitable gas.

Capsules and cartridges for use in an inhaler or insufflator, of for example gelatin, may be formulated containing a powder mix of a compound of the invention and a suitable powder base such as lactose or starch.

The pharmaceutical compositions according to the invention may also be used in combination with other therapeutic agents, for example anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), lung surfactants and/or antimicrobial and anti-viral agents. The compositions according to the invention may also be used in combination with gene replacement therapy.

The invention thus provides, in a further aspect, a combination comprising a compound of formula (I) or a physiologically acceptable salt or solvate thereof together with another therapeutically active agent.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

The compound of the invention may conveniently be administered in amounts of, for example, 0.01 to 50 mg/kg body weight, suitably 0.05 to 25 mg/kg body weight orally, one or more times a day. The precise dose will of course depend on the age and condition of the patient, the particular route of administration chosen, and the disease being treated. The compound is preferably administered orally for the treatment of bronchitis. Other routes of administration may be needed for other indications, for instance i.v. for ARDS.

The compounds of the invention have useful duration of action.

The compounds of formula (I) and salts and solvates thereof may be prepared by the methodology described hereinafter, constituting a further aspect of this invention.

A process according to the invention for preparing a compound of formula (I) comprises:

(i) condensation of a compound of formula (II):

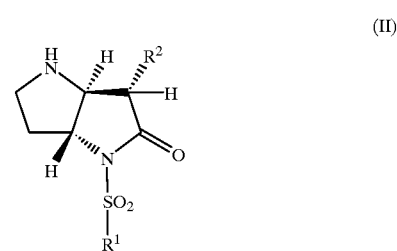

(II)

(relative stereochemistry indicated)

with a compound of formula (XXXX)

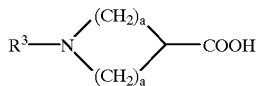
(XXXX)

or an acid derivative thereof, e.g. an acid halide such as the acid chloride, or a protected derivative thereof, or (ii) sulphonylation of a compound of formula (III):

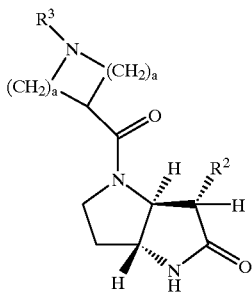
(III)

(relative stereochemistry indicated)

or a protected derivative thereof with a compound $YO_2SR^1$ wherein Y is a reactive group such as halogen, e.g. chlorine; or (iii) cyclising a compound of formula (IV):

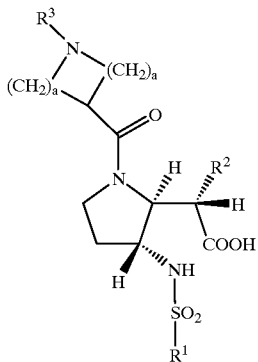
(IV)

(relative stereochemistry indicated)

or a carboxylic acid ester thereof; or (iv) oxidation of a corresponding compound of formula (V)

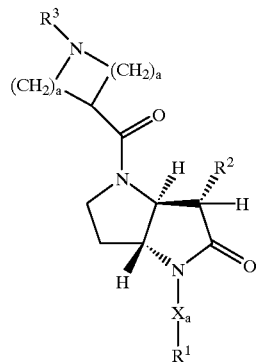
(V)

(relative stereochemistry indicated)
wherein $X_a$ is sulphur or SO; or
(v) reaction of a corresponding compound of formula (VI)

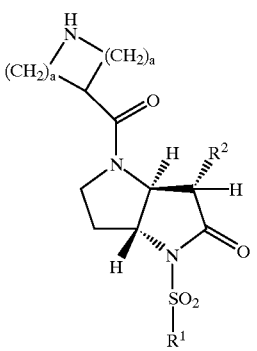
(VI)

(relative stereochemistry indicated)
with a compound of formula $R^3$-L
wherein L is a leaving group; or
(vi) deprotecting a protected derivative of a compound of formula (I); or
(vii) purifying one enantiomer of the compound of formula (I) from a mixture of enantiomers;
and where desired or necessary converting a resultant free base compound of formula I into a physiologically acceptable salt form or vice versa or converting one salt form into another physiologically acceptable salt form.

Process (i)

This condensation reaction is suitably carried out in the presence of a coupling agent such as EDC, HATU or TBTU, preferably also in the presence of HOBT, and a solvent such as dichloromethane, DMF, MeCN or tetrahydrofuran at a temperature of suitably between 0° C. and ambient. It will be appreciated that as an alternative to using a carboxylic acid, acid derivatives such as the acid chloride, activated ester, acid anhydride, or a mixed anhydride may be used. Reaction conditions will be modified accordingly, for instance by inclusion of a base.

Process (ii)

The sulphonylation reaction is suitably carried out in the presence of LHMDS or NaH, in a solvent such as tetrahydrofuran at a temperature of suitably between −78° C. and 0° C.

Process (iii)

The cyclisation reaction is suitably carried out in the presence of 2-chloro-1-methylpyridinium iodide or EDC in a solvent such as dichloromethane, at a temperature of suitably 0° C.—reflux. Acid derivatives including acid halides (eg acid chlorides) (preferably in the presence of a base), anhydrides, thioesters may also be used in this reaction.

Process (iv)

This oxidation reaction may be carried out in conventional manner such as by peracid oxidation.

Process (v)

Preferred leaving groups include halogen (such as chlorine, bromine or iodine), mesylate and tosylate. The reaction may be performed by combining the reactants optionally in the presence of a base such as triethylamine or potassium carbonate in an inert aprotic solvent such as DMF or MeCN.

Process (vi)

Protecting groups, especially nitrogen protecting groups, and means for deprotection are described in T W Greene "Protective Groups in Organic Synthesis", 2nd Ed (1991) J Wiley & Sons.

Process (vii)

Purification of a single enantiomer may be achieved by conventional methods such as chiral chromatography (e.g. chiral HPLC) and crystallisation using a homochiral acid (e.g. tartaric acid).

Physiologically acceptable acid salts of the compound of formula (I) such as the hydrochloride or tartrate may be prepared by treating a basic compound of formula (I) with the desired acid.

Compounds of formula (I) in which $R^3$ represents $C_{2-8}$ alkyl or $-(CH_2)_n Ar$ may also be prepared by reductive amination of a compound of formula (VI).

For this reductive amination reaction, the compound of formula (VI) may first be treated with a corresponding aldehyde, followed by reduction with a reducing agent such as triacetoxyborohydride typically in the presence of acetic acid in an inert solvent such as DCM.

Intermediate compounds of formula (II) may conveniently be prepared according to the methodology in Scheme I below:

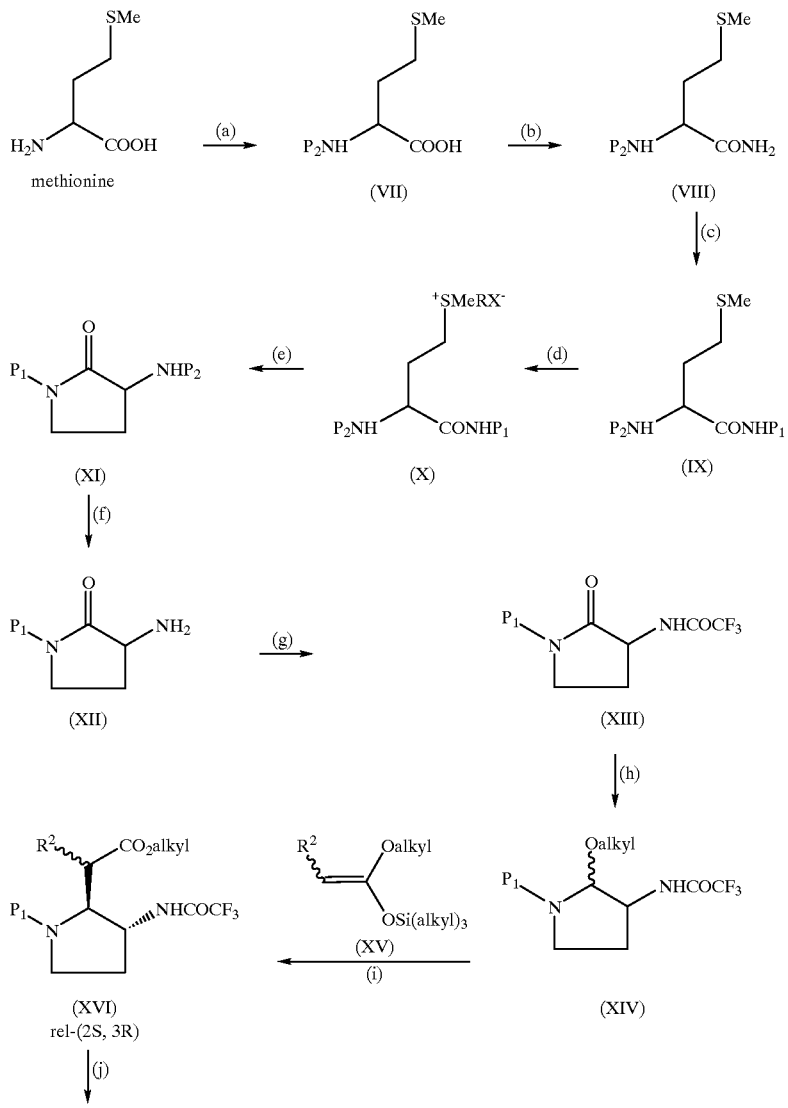

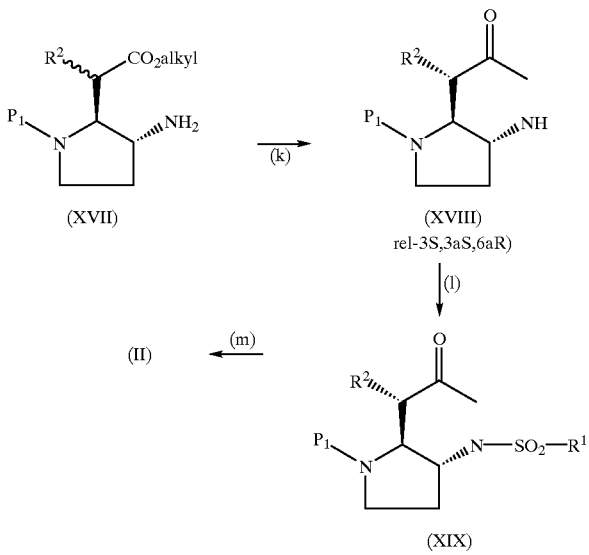

Step (a)
This is a conventional protection reaction which, in the case when $P_2$ represents BOC, may be performed by reacting with $(BOC)_2O$ in the presence of base (e.g. NaOH) in a polar solvent system such as dioxan/water.

Step (b)
This conversion may be performed on treatment with ammonium bicarbonate in the presence of a suitable solvent such as pyridine/DMF and in the presence of $(BOC)_2O$ or suitable equivalent.

Step (c)
This is a conventional protection reaction which, in the case when $P_1$ represents CBZ, may be performed by reaction with nBuLi followed by CBZ-Cl in the presence of an inert solvent such as THF below $-50°$ C.

Step (d)
This reaction may be performed by treatment with RX where RX is a compound (e.g. MeI, benzyl iodide or $Me_2SO_4$) capable of converting sulphur in the SMe moiety into sulphonium in a suitable solvent, e.g. propanone or acetonitrile. Generally R will represent alkyl or aralkyl and X will represent halide especially iodide or sulphate. Protection of the amide is convenient, although not essential, for this reaction.

Step (e)
This ring closure reaction may be performed by treatment with Dowex 2X8 400 mesh OH⁻ resin in a suitable solvent, e.g. MeCN. Alternatively, the ring closure may be performed by treatment with potassium carbonate in a suitable solvent e.g. MeCN.

Step (f)
Deprotection may be performed in a conventional manner, for example, a BOC protecting group may be removed by treatment with HCl, e.g. in dioxan.

Step (g)
This reaction may be performed by treatment with a trifluoroacetic acid alkyl ester (e.g. the methyl ester) or trifluoroacetic anhydride in the presence of a suitable base e.g. N-methylmorpholine.

Step (h)
This conversion will take place on treating the compound of formula (XIII) with a reducing agent e.g. lithium borohydride, followed by treatment with concentrated sulphuric acid in the presence of an alkyl alcohol e.g. ethanol solvent.

Step (i)
The reaction of compounds of formula (XIV) and (XV) takes place in the presence of a Lewis acid e.g. boron trifluoride dietherate and an inert solvent e.g. dichloromethane. The group "alkyl" in Oalkyl and $OSi(alkyl)_3$ generally represents $C_{1-6}$alkyl. In the compound of formula (XV), suitable alkyl groups in the silyl alkyl moiety include methyl, isopropyl and t-butyl Preferred Oalkyl is OEt and preferred $OSi(alkyl)_3$ is $OSi(i-Pr)_3$ or $OSi(Me)_2(t-Bu)$. The use of variants of compounds of formula (XV) in which Oalkyl is replaced by $OSi(alkyl)_3$ is also envisaged.

Compounds of formula (XV) may be prepared by treatment of the corresponding carboxylic acid ester ($R^2CH_2COOEt$ or another alkyl ester, which compounds are either known or may be prepared by known methods) with a strong base (eg LHMDS) followed by a trialkylsilylchloride (such as trimethylsilylchloride) or a trialkylsilyltriflate. Typically the reaction will be performed at low temperature (less than $0°$ C.) in an inert solvent (such as THF) in the presence of DMPU.

Step (j)
This deprotection reaction will take place on treatment with base, such as potassium carbonate.

Step (k)
This ring closure reaction may be performed on treatment with an alkyl Grignard reagent (eg t-butylmagnesium choride) in an inert solvent such as THF in the presence of tetramethylethylenediamine at a temperature of $-20°$ C. to $25°$ C.

Step (l)
This is a lactam sulphonylation reaction. It is suitably carried out by reaction with $R^1SO_2$—Y, wherein Y is a reactive group, preferably chloro, in the presence of LHMDS, NaH or KH, in a solvent such as THF, at a temperature of suitably $-78°$ to $0°$ C.

Step (m)
This is an N-deprotection reaction, which can suitably be carried out in conventional manner. Thus when $P_1$ is CBZ, it is suitably carried out by hydrogenation over Pd $(OH)_2$ catalyst in solvents such as ethyl acetate or THF.

Compounds of formula (XIII) may also be prepared by following a route described in Scheme 2:

Scheme 2

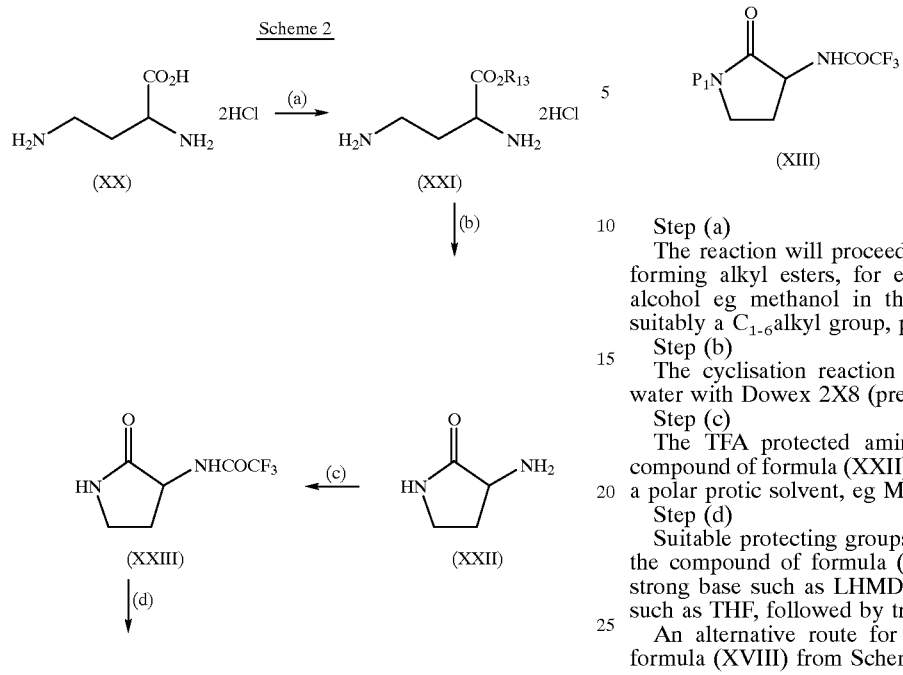

Step (a)
The reaction will proceed under standard conditions for forming alkyl esters, for example by treatment with an alcohol eg methanol in the presence of $SOCl_2$. $R_{13}$ is suitably a $C_{1-6}$alkyl group, preferably methyl.

Step (b)
The cyclisation reaction will take place on stirring in water with Dowex 2X8 (preferably 400 mesh).

Step (c)
The TFA protected amine is formed by treating the compound of formula (XXII) with methyl trifluoroacetate in a polar protic solvent, eg MeOH.

Step (d)
Suitable protecting groups $P_1$ include CBZ. In this case, the compound of formula (XXIII) may be treated with a strong base such as LHMDS or nBuLi in an inert solvent such as THF, followed by treatment with CBZ-Cl.

An alternative route for preparation of compounds of formula (XVIII) from Scheme 1 is given in Scheme 3:

Scheme 3

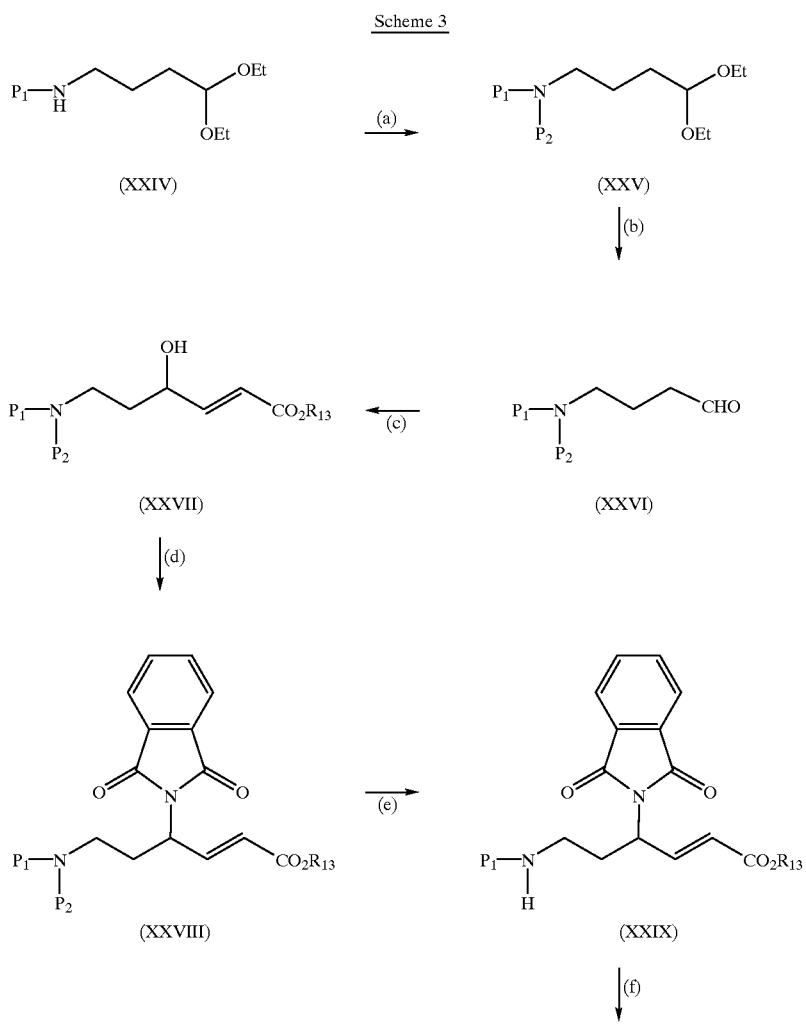

-continued

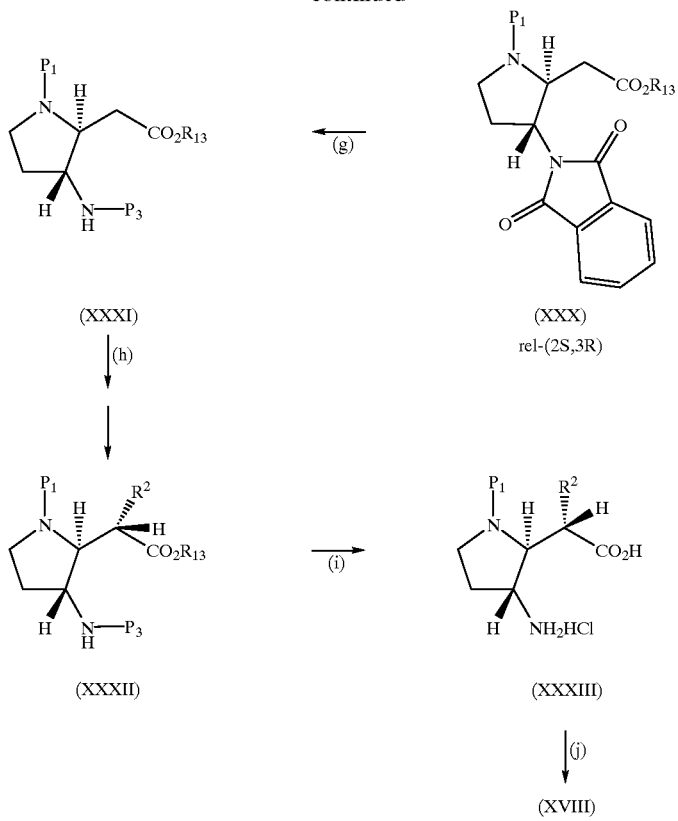

(XXXI)

(XXX) rel-(2S,3R)

(XXXII)

(XXXIII)

(XVIII)

Step (a)

The compounds of formula (XXIV) are either known compounds or may be made in analogous manner to known compounds. $P_1$ is an N-protecting group, preferably CBZ. Step (a) is a further N-protection reaction. $P_2$ in formula (XXV) is a different N-protecting group, preferably BOC. When $P_2$ is BOC, the reaction is suitably carried out using $BOC_2O$.

Suitably the reaction is carried out in the presence of a base such as triethylamine or 4-dimethylaminopyridine in a solvent such as ethyl acetate, at temperature of suitably 0°–25° C.

Step (b)

This conversion is suitably carried out with pyridinium p-toluenesulfonate, in a solvent such as acetone/water, at a temperature suitably between $25°–75°$ C.

Step (c)

This is a condensation rearrangement reaction suitably carried out using a 2-phenylsulfinyl acetic acid ester ($PhSOCH_2$ $CO_2R_{13}$) and piperidine, in a solvent such as acetonitrile, suitably at ambient temperature. $R_{13}$ is suitably a $C_{1-6}$alkyl group, preferably methyl.

Step (d)

This is a Mitsunobu substitution reaction, using phthalimide, $PPh_3$ and a dialkylazodicarboxylate such as DEAD, in the presence of a solvent such as THF, at a temperature of suitably 0°–40° C.

Step (e)

This is a deprotection reaction, preferably using a strong acid such as TFA in a solvent such as DCM, at a temperature of suitably 0°–40° C. $R_{13}$ is suitably $C_{1-6}$alkyl, preferably ethyl.

Step (f)

This is a cyclisation reaction, suitably carried out as an intramolecular Michael reaction. Suitably NaH is used, in a solvent such as THF, at a temperature such as 0°–25° C.

Step (g)

In this step two reactions occur: N-deprotection and re-protection. The phthalimido group is removed suitably with hydrazine hydrate in a solvent such as ethanol at a temperature between 0° C. and reflux. Protecting group $P_3$ is incorporated in a conventional manner. When $P_3$ is BOC, this is suitably achieved with $BOC_2O$.

Step (h)

The $R^2$ side chain may be introduced by alkylation, using as reactant $R^2$—Y, wherein Y is a reactive group such as bromo or iodo. Thus the reaction is carried out using a base, preferably a strong base such as LHMDS. With LHMDS suitably a cosolvent DMPU in THF is used. Suitable reaction temperatures are −78° to 50° C. Under these conditions the reaction generally takes place with good stereochemical control.

Step (i)

This is an ester hydrolysis reaction, followed by an N-deprotection reaction. The former is carded out in a conventional manner, for example by using KOH in aqueous ethanol, at a temperature of suitably 25°–80° C. The latter is carried out in a conventional manner, for example by using HCl in dioxan, at a temperature of suitably 0°–50° C. or, if the protecting group is trifluoroacetate by treatment with base, Step (j)

This is a cyclocondensation reaction, suitably carried out in the presence of 2-chloro-1-methylpyridinium iodide and a suitable base such as N, N-diisopropyl ethylamine in a solvent such as dichloromethane, at a temperature of suitably 0° C.-reflux. We have also found that it is possible to use the compound of formula (XXXIII) as a carboxylic acid ester in which case the ester hydrolysis of step (i) is not necessary. In this case the preferred conditions for the cyclocondensation reaction involve the use of an alkyl Grignard reagent eg t-BuMgCl in THF at a temperature between −20° C. and 25° C.

An alternative process for preparation of compounds of formula (XXXI) is shown in Scheme 4:

Step (c)
This reaction is suitably carried out in two stages. The first stage involves reacting the compound of formula (XXXVI) at reduced temperature with N-methylmorpholine and then an alkyl chloroformate such as ethyl chloroformate, in an organic solvent such as DCM, dioxan or THF. In the second stage the product is reduced, suitably with sodium borohydride at a reduced temperature, such as −20° to 10° C., in a solvent such as THF.

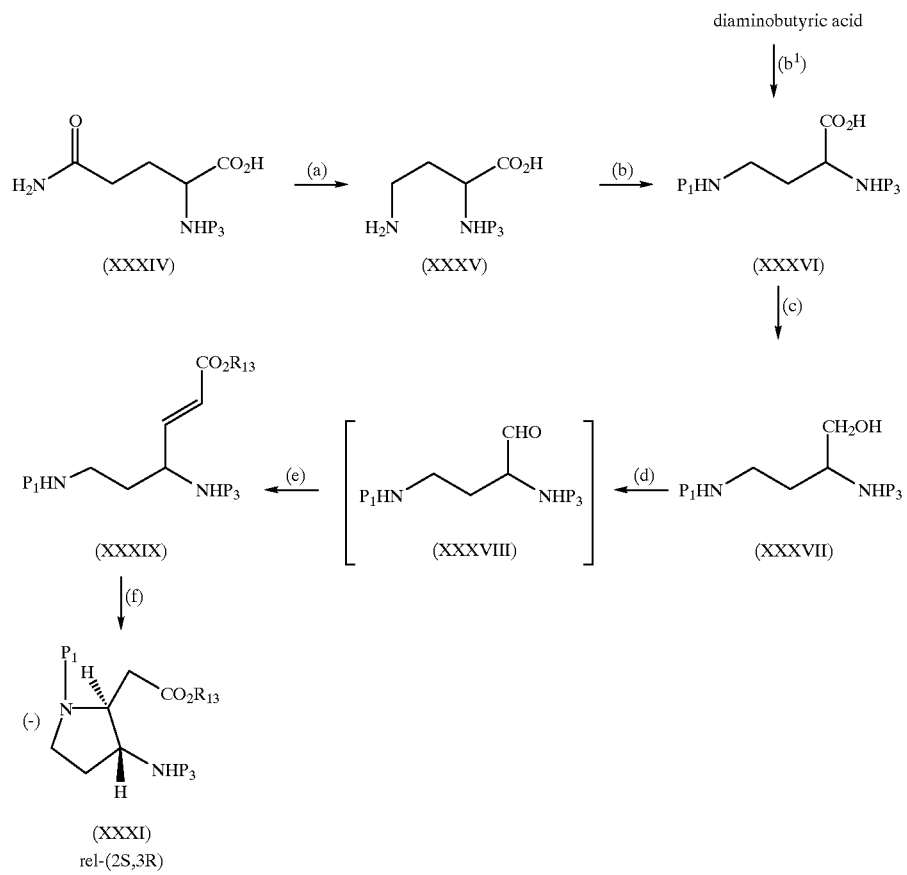

Step (a)
The compounds of formula (XXXIV) are either known compounds or may be prepared in analogous manner to known compounds. $P_3$ is a protecting group as discussed above, and is suitably BOC. The reaction is suitably carried out using PIFA (phenyl iodosylbis(trifluoroacetate)) and a base such as pyridine in an aqueous solvent, such as aqueous THF, dioxan or acetonitrile. This is the method of Stansfield, C. F. Organic Preparations and Procedures Int., 1990, 22(5), 593–603.

Step (b)
$P_1$ is a protecting group eg CBZ. This protection reaction may be carried out in a conventional manner. For instance it is suitably carried out in a water miscible solvent such as THF, DMF or dioxan using N-(benzyloxycarbonyloxy) succinamide, benzyloxycarbonyl chloride, or any suitable source of the benzyloxycarbonyl group, with pH adjustment to alkaline with sodium carbonate.

As an alternative step ($b^1$), the compound of formula (XXXVI) can be prepared in conventional manner from diaminobutyric add.

Step (d)
This oxidation reaction may be carried out in any suitable manner, for instance using oxalyl chloride in DMSO and DCM under nitrogen at reduced temperature, such as −30° to −70° C., followed by triethylamine. The intermediate (XXXVIII) suitably is not isolated.

Step (e)
This reaction is suitably carried out using a Wittig reagent such as a triphenylphosphorane $R_{13}O_2CCH=PPh_3$, or may also be carried out using a phosphonate in a Wadsworth-Emmons reaction.

Step (f)
This Michael addition reaction is suitably carried out using LHMDS or other suitable strong base in a suitable organic solvent such as THF, ether or toluene, and preferably a complexing agent such as TMEDA is also present.

The intermediate compounds of formula (III) may be prepared by reacting a deprotected compound of formula (XVIII) from Scheme 1 with a compound of formula (XXXX)

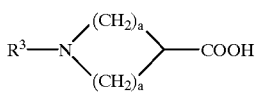
(XXXX)

or an acid derivative thereof such as an acid halide (e.g. the acid choride) in the manner described above in relation to main process (i) above.

(The initial N- deprotection may be carried out as described above under Scheme 1 Step (m)).

The intermediate compounds of formula (IV) may be prepared from a compound of formula (XVII) (with the primary amine suitably protected) in an analogous manner to that described above for preparing a compound of formula (III) from a compound of formula (XVIII) together with main process (ii) above.

Compounds of formula (V) wherein $X_a$ represents S may be prepared by reaction of a corresponding compound of formula (III) with a compound of formula $R^1SSR^1$ under standard conditions for nucleophilic displacement. Compounds of formula (V) wherein $X_a$ represents SO may be prepared by peracid oxidation of a corresponding compound wherein $X_a$ represents S.

Compounds of formula (VI) may be prepared by a process comprising reacting a compound of formula (II) with a compound of formula (XXXXA)

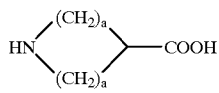
(XXXXA)

or an acid derivative such as an acid halide (e.g. acid chloride) or a protected derivative thereof, following conventional methods known per se.

Compounds of formula (XXXXA) will generally be used in protected form e.g. N-protected by CBZ.

Compounds of formula (XXXX) and (XXXXA) are either known or may be prepared by conventional methods known per se.

More specifically compounds of formula (XXXX) in which $R^3$ represents $C_{2-8}$ alkyl or —$CH_2)_nAr$ may be prepared by reductive amination of a compound of formula (XXXXA) under conventional conditions.

Also, by way of example, compounds of formula (XXXX) or (XXXXA) may be prepared by hydrolysis of a corresponding nitrile compound, which may be prepared from the corresponding hydroxy compound. This chemistry is illustrated for compounds in which a represents 1 in Anderson and Lok (1972), J Org. Chem. 37 (24) 3953–3955 and references mentioned therein.

It will be apparent that Schemes 1, 2, 3 and 4 may be modified to produce homochiral products by using homochiral starting materials (e.g. S-methionine in Scheme 1 or S-diaminobutyric acid in Scheme 4) or by performing an additional chiral resolution step.

If compounds of formula (XII) in racemic form are prepared following Scheme 1 from racemic methionine, we have found that the isomers of the compounds of formula (XII) may be resolved by a dynamic resolution procedure. Thus a racemic compound of formula (XII) may be treated with homochiral di-p-toluoyl tartaric acid in the presence of 3,5-dichloro-2-hydroxybenzaldehyde as catalyst in an inert solvent, e.g. THF. A homochiral salt of the compound of formula (XII) results. A compound of formula (XIII) may then be produced by subsequent treatment with trifluoroacetic acid methyl ester in the presence of N-methylmorpholine.

Both enantiomers of the compound of formula (XII) may also be produced from a synthesis based on S-methionine following a similar procedure.

It will be apparent to a person skilled in the art that the above synthetic processes for the preparation of compounds of formula (I) may be modified so as to include or omit protecting groups or so as to use alternative protecting groups (for example those described in T W Greene "Protective Groups in Organic Synthesis", 2nd Ed (1991) J Wiley & Sons) in the course of routine optimisation of experimental conditions.

Novel chiral intermediates in the above described chiral and resolution sections also form an important aspect of this invention.

Processes for preparation of intermediates are also provided as an aspect of this invention.

The compounds of the invention have the advantage that they may be more efficacious, show greater selectivity, have fewer side effects, have a longer duration of action, be more bioavailable by the preferred route, have more attractive pharmacodynamic or pharmacokinetic properties or have other more desirable properties than similar known compounds.

The following non-limiting Examples illustrate the present invention.

ABBREVIATIONS

BOC t-butyloxycarbonyl
CBZ Benzyloxycarbonyl
(BOC)$_2$O Di-tert-butyidicarbonate
THF Tetrahydrofuran
LHMDS Lithium bis (trimethylsilyl)amide
DMPU 1,3-dimethyl-3,4,5,6-tetrahydro 2 (1H)-pyrimidinone
DMAP 4-dimethylaminopyridine
DMF Dimethylformamide EDC 1-(3-N,N-dimethylaminopropyl)-3-ethylcarbodiimide
DEAD diethylazodicarboxylate
DCM dichloromethane
TMEDA tetramethylethylenediamine
HOBT 1-hydroxybenzotriazole
HATU O-(7-azabenzotriazol-1-yl)-1,1,3,3,-tetramethyluronium hexafluorophosphate
TBTU 2-(1H-benzotriazole-1-yl)-1,1,3,3-tetra methyluronium tetrafluoroborate
DMSO dimethylsuiphoxide
Intermediates
Intermediate 1: 2,4-Diamino-butyric acid methyl ester dihydrochloride To D,L-diaminobutyric acid dihydrochloride (350 g) in methanol (1.61) at 0° C. was added thionyl chloride (200 ml) over ½ h. After reflux for 3 h, the solvent was removed in vacuo and the residue triturated with toluene (650 ml) to give the title compound as a white solid (385 g).

Mass spec. of free base MH⁺ (found) 133 MH⁺ (calculated) 133

Intermediate 2: 3-Amino-pyrrolidin-2-one

Intermediate 1 (1 g), water (70 ml) and Dowex 2X8-400 mesh (16.4 ml) were stirred for 1 h. The resin was then filtered off and the filtrate concentrated in vacuo to give the title compound as a white solid (0.40 g), T.l.c silica (18:3 ethyl acetate: methanol) Rf 0.07.

Intermediate 3: 2,2,2-Trifluoro-N-(2-oxo-pyrrolidin-3-yl)-acetamide

A suspension of Intermediate 2 (181 g), methyl trifluoroacetate (218 ml) and methanol (2.6 l) was stirred for 2 h. The solvent was then removed in vacuo to afford the title compound as a cream solid (355 g). Mass spec. $MNH_4^+$ (found) 214 $MNH_4^+$ (calculated) 214

Intermediate 4: 2-Oxo-3-(2,2,2-trifluoro-acetylamino)-pyrrolidine-1-carboxylic acid benzyl ester To Intermediate 3 (3.5 g) in tetrahydrofuran (100 ml) at −70° C. was added lithium hexamethyldisilazide (20 ml). After ¼ h, benzyl chloroformate (2.8 ml) was added. The mixture was warmed to room temperature for 1 h and 1 M hydrochloric acid (25 ml) added. After extraction with ethyl acetate (3×25 ml), the combined extracts were washed with 2% ammonia solution, 2M hydrochloric acid and brine, then dried ($MgSO_4$). After solvent removal, the white solid was recrystallised from ethyl acetate: hexane 5:1 to give the title compound (4.2 g), T.l.c. silica (18:2 ethyl acetate: methanol) Rf 0.7.

Intermediate 5: 2-Ethoxy-3-(2,2,2-trifluoro-acetylamino)-pyrrolidine-1-carboxylic acid benzyl ester To Intermediate 4 (34 g) in ethanol (1070 ml) at −5° C. was added sodium borohydride (9.86 g). A solution of 4M hydrogen chloride in 1,4-dioxan (20 ml) was then added dropwise. Periodically further portions of 4M hydrogen chloride in 1,4-dioxan (2×5 ml, 1×10 ml) and sodium borohydride (2 g) were added. After 3 h, concentrated sulphuric acid (11 ml) was added and the mixture warmed to room temperature for 2 h. Saturated aqueous sodium bicarbonate (300 ml) was then added and the ethanol and dioxan removed in vacuo. The residue was diluted with water (500 ml) and extracted with ethyl acetate (3×500 ml). The combined extracts were washed with brine and dried ($MgSO_4$). The solvent was removed in vacuo and the residue purified by flash chromatography on silica gel 9385 eluting with ether, to give the title compound (21 g). Mass spec. $MNH_4^+$ (found) 378 $MNH_4^+$ (calculated) 378

Intermediate 6: trans-2-(1-Ethoxycarbonyl-2-methyl-propyl)-3-(2,2,2-trifluoro-acetylamino)-pyrrolidine-1-carboxylic acid benzyl ester Intermediate 5 (10 g), ethyl trimethylsilyl isopropylketene acetal (11 ml) and dichloromethane (250 ml) were cooled to 5° C. and boron trifluoride dietherate (17 ml) added over ¼ h. After 1 h, further boron trifluoride dietherate (3.4 ml) and ketene acetal (11 ml) were added. After a further 1 h, 1 M hydrochloric acid (200 ml) was added and the organic layer separated and washed with brine and dried ($MgSO_4$). Solvent removal in vacuo gave the title compound (16.7 g), T.l.c. silica (2:1 ether. cyclohexane) Rf 0.18 and 0.27.

Intermediate 7: trans-3-Amino-2-(1-ethoxycarbonyl-2-methyl-propyl)-pyrrolidine-1-carboxylic acid benzyl ester Intermediate 6 (31 g), potassium carbonate (71 g), water (930 ml) and ethanol (930 ml) were warmed at 60° C. for 3 h. The ethanol was removed in vacuo and the aqueous residue extracted with ethyl acetate (3×300 ml). The combined extracts were washed with brine and dried ($MgSO_4$) and concentrated in vacuo to give the title compound as a brown oil (17.5 g).

Mass spec. $MH^+$ (found)) 349 $MH^+$ (calculated) 349

Intermediate 8: rel-(3R,3aR,6aS)-6-lsopropyl-5-oxo-hexahydro-pyrrolo[3,2-b]pyrrole-1-carboxylic acid benzyl ester Intermediate 7 (17.5 g) in tetrahydrofuran (1,800 ml) was cooled to −5° C. and 1M t-butylmagnesium chloride in tetrahydrofuran(204 ml) was added over ½ h. After 2 h, 1M hydrochloric acid (250 ml) and brine (300 ml) were added. The mixture was then extracted with ethyl acetate (250 ml). After concentrating the extracts to half volume in vacuo, the extracts were washed with brine and dried ($MgSO_4$). Solvent removal in vacuo followed by trituration with diethyl ether (60 ml) gave a white solid. This was recrystallised from ethyl acetate to give the title compound (3.4 g). Mass spec. $MH^+$ (found) 303 $MH^+$ (calculated) 303

Intermediate 9: rel-(3R,3aR,6aS)-6-Isopropyl-4-methanesulfonyl-5-oxo-hexahydro-pyrrolo[3,2-b]pyrrole-1-carboxylic acid benzyl ester To a stirred solution of Intermediate 8 (15.01 g) in anhydrous tetrahydrofuran (950 ml) at −74° C. under nitrogen, was added 1.0M lithium hexamethyldisilazide in tetrahydrofuran (69.5 ml) dropwise. After stirring at −74° C. for 10 min, the mixture was allowed to warm to 0° C. over 45 min, then left at this temperature for 20 min. It was then cooled to −76° C., treated dropwise with methanesulfonyl chloride (9.61 ml) and left to stir at this temperature for 1.5 h. It was then warmed to −50° C., quenched with saturated ammonium chloride solution (480 ml) and allowed to warm up to room temperature. The mixture was partitioned between water (300 ml) and ethyl acetate (750 ml), the aqueous layer extracted with further ethyl acetate (750 ml), then the combined organic extracts washed with brine (450 ml), dried ($Na_2SO_4$) and concentrated in vacuo to a cream solid. Purification by flash column chromatography on silica (Merck 9385) eluting with ethyl acetate: cyclohexane (1:3, 1:2, 1:1 then 3:1) gave the title compound as a white crystalline solid (13.65 g). Tlc silica (dichloromethane) Rf 0.22 Mass spec $MNH_4^+$ (found) 398 $MNH_4^+$ (calculated) 398

Intermediate 10: rel-(3R,3aR,6aS)-3-lsopropyl-1-methanesulfonyl-hexahydro pyrrolo[3,2-b]pyrrol-2-one A suspension of Intermediate 9 (13.63 g) in ethyl acetate (900 ml) was added to 20% palladium hydroxide (moist) on carbon (3.16 g) and the resulting black suspension stirred vigorously under hydrogen at room temperature for 90 min. The mixture was then filtered through Harborlite J2 and concentrated in vacuo to give the title compound as a fine white powder (8.63 g). Tlc silica (Methanol: dichloromethane 1:9) Rf 0.50 Mass spec $MH^+$ (found) 247 $MH^+$ (calculated) 247

Intermediate 11: rel-(3R,3aR,6aS)-3-6-Isopropyl-4-methanesulfonyl-5-oxo-hexahydro-pyrrolo[3,2-b]pyrrole-1-carbonyl)-azetidine-1-carboxylic acid benzyl ester 1-Benzyloxycarbonyl azetidine-3-oic acid (0.235 g), Intermediate 10 (0.246 g), 1-(3-dimethylamino propyl)-3-ethyl-carbodiimide hydrochloride (0.230 g) and acetonitrile (5 ml) were stirred at room temperature for 6 h. The solvent was removed in vacuo and replaced with ethyl acetate (25 ml). The solution was washed with 1M hydrochloric acid (2×25 ml), 8% bicarbonate solution (25 ml)) and brine (10 ml) and dried ($MgSO_4$). Solvent removal in vacuo gave the title compound as a colourless oil (0.392 g). Mass spec $MNH_4^+$ (found) 481, $MNH_4^+$ (calc) 481

Intermediate 12: rel-(3R,3aR,6aS)-4-(Azetidine-3-carbonyl)-3-isopropyl-1-methanesulfonythexahydro-pyrrolo[3,2-b]pyrrol-2-one acetate A solution of Intermediate 11 (0.090 g) in acetic acid (15 ml), was hydrogenated over platinum oxide catalyst (0.227 g) for 3 h. The catalyst was then filtered off and the filtrate concentrated in vacuo. The residue was azeotroped with toluene (100 ml) to afford the title compound as an oil (0.077 g). Mass spec $MH^+$ (found) 330, $MH^+$ (calc) 330

Intermediate 13: 1-benzyloxycarbonyl azetidine-3-oic acid

To azetidine-3-carboxylic acid (0.50 g), potassium carbonate (0.82 g), dioxan (5 mL), water (10 mL) was added benzyl chloroformate (0.74 mL) at room temperature for 6 h under nitrogen. Piperazine (5 drops) was then added. After ½ h, the dioxan was removed in vacuo and the residue diluted with 2M hydrochloric acid (25 mL). After extracting with ethyl acetate (35 mL), the organic layer was washed with brine (10 mL) and dried (MgSO$_4$). Solvent removal in vacuo gave Intermediate 13 as a colourless oil (1.07 g).

Mass spec MNH$_4^+$ (found) 253, MNH$_4^+$ (calc) 253

Intermediate 14: (3S,3aS,6aR)-3-(6-isopropyl-4-methanesulfonyl-5-oxohexahydro-pyrrolo[3,2-b]pyrrole-1-carbonyl)-azetidine-1-carboxylic acid benzyl ester A mixture of (3S,3aS,6aR)-3-Isopropyl-1-methanesulfonyl-hexahydro-pyrrolo[3,2-b]pyrrol-2-one (Intermediate 122 from International Patent Application WO97/36903) (0.90 g), 1-(3-dimethylaminopropyl)-3-ethylcarbodiimide (0.91 g) and acetonitrile (12 mL) were stirred for 5 min under nitrogen after which Intermediate 13 (0.90 g) in acetonitrile (30 mL) was added. After 18 h the solvent was removed in vacuo and the residue treated with 2M hydrochloric acid (30 mL) and extracted with ethyl acetate (90 mL). The organic layer was washed with 2M hydrochloric acid (30 mL), saturated sodium bicarbonate solution (2×30 mL), brine (30 mL) and dried (MgSO$_4$) and concentrated in vacuo. The residue was purified by flash chromatography on silica (Merck 9385) eluting with 10% then 20% acetonitrile in dichloromethane to give Intermediate 14 as a colourless foam (0.80 g).

Mass spec MH$^+$ (found) 464, MH$^+$ (calc) 464

Intermediate 15: (3S,3aS,6aR)-4-(azetidine-3-carbonyl)-3-isopropyl-1-methanesulfonyl-hexahydropyfrolo[3,2-b]pyrrol-2-one acetate.

Platinum (IV) oxide (1.0 g) and acetic acid (50 mL) were prehydrogenated for ½ h and then Intermediate 14 (0.30 g) in acetic acid (50 mL) was added. After vigorous stirring under hydrogen for 19 h the reaction was filtered through a 3M Empore C18 extraction disc cartridge and concentrated in vacuo. The residual gum was azeotroped with toluene (3×50 mL) and triturated with ether (2×20 mL) to give lntermdiate 15 as a white powder (0.63 g).

Mass spec MH$^+$ (found) 330, MH$^+$ (calc) 330

EXAMPLES

Example 1 rel-(3R,3aR,6aS)-4-(1-CyclopropyImethyl-azetidine-3carbonyl)-3-isopropyl-1-methanesulfonyl-hexahydropyrrolo[3,2-b]pyrrol-2-one hydrochloride Intermediate 12 (0.019 g), acetic acid (1 drop), sodium triacetoxyborohydride (0.021 g), cyclopropanecarboxaldehyde (0.075 ml) and dichloromethane (1 ml) were stirred at room temperature for 3 days. The mixture was diluted with dichloromethane (5 ml), stirred with 8% sodium bicarbonate solution (5 ml) and separated. Concentration of the organic layer followed by purification by preparative thin layer chromatography eluting with dichloromethane:ethanol: ammonia 100:8:1 afforded a colourless oil (0.007 g). This was dissolved in chloroform (1 ml). 1M Hydrogen chloride in ether (1 ml) was added and the solvents removed in vacuo to afford the title compound as a white solid (0.009 g). T.l.c Silica dichloromethane: ethanol:ammonia [100:8:1], Rf 0.39

Mass spec MH$^+$ (found) 384, MH$^+$ (calc) 384

Example 2 rel-(3R,3aR,6aS)-4-(1-Benzylazetidine-3-carbonyl)-3-isopropyl-1-methanesulfonyl-hexahydro-pyrrolo[3,2-b]pyrrol-2-one hydrochloride Example 2 was similarly prepared to Example 1 from Intermediate 12 and benzaldehyde (0.011 ml) to afford the title compound as a white solid (0.009 g). T.l.c SiO$_2$ Dichloromethane:ethanol:ammonia [100:8:1], Rf 0.46

Mass spec MH$^+$ (found) 420, MH$^+$ (calc) 420

Example 3 rel-(3R,3aR,6aS)-4-[1-(2,2-Dimethyl-propyl)-azetidine-3-carbonyl]-3-isopropyl-1-methanesulfonyl-hexahydro-pyrrolo[3,2-b]pyrrol-2-one hydrochloride Example 3 was similarly prepared to Example 1 from Intermediate 12 and pivaldehyde (0.011 ml) to afford the title compound as a white solid (0.010 g). T.l.c SiO$_2$ Dichloromethane:ethanol:ammonia [100:8:1] Rf 0.44 Mass spec MH$^+$ (found) 400, MH$^+$ (calc) 400

Example 4 rel-(3R,3aR,6aS)-4-[1-(2,6-Dichloro-benzyl)-azetidine-3-carbonyl]-3-isopropyl-1-methanesulfonyl-hexahydropyrrolo[3,2-b]pyrrol-2-one hydrochloride Example 4 was prepared similarly to Example 1 from Intermediate 12 and 2,6-dichlorobenzaldehyde (0.017 g) to afford after trituration with ether (3×1 ml) the title compound as a white solid (0.003 g). T.l.c SiO$_2$ Dichloromethane:ethanol: ammonia [100:8:1], Rf 0.51 Mass spec MH$^+$ (found) 488, 490, MH$^+$ (calc) 488,490

Example 5 rel-(3R,3aR,6aS)-4-(1-Butyazetidine-3-carbonyl)-3-isopropyl-1-methanesulfonyl-hexahydro-pyrrolo[3,2-b]pyrrol-2-one hydrochloride Example 5 was similarly prepared to Example 1 from Intermediate 12 and butyraldehyde (0.009 ml) to afford the title compound as a white solid (0.006 g). T.l.c SiO$_2$ Dichloromethane:ethanol:ammonia:[100:8:1], Rf 0.46

Mass spec MH$^+$ (found) 386, MH$^+$ (calc) 386

Example 6

(3S, 3aS, 6aR)-4-[1-(2,2-Dimethylpropyl)-azetidine-3-carbonyl]-3-isopropyl-1-methanesufonyl-hexahydropyrrolo[3,2-b]pyrrol-2-one To Intermediate 15 (0.625 g) in dichloromethane (90 mL) was added acetic acid (9 drops—ca 100 µL), sodium triacetoxyborohydride (0.680 g) and pivaldehyde (0.24 mL). After 18 h, the mixture was concentrated in vacuo and the residue treated with ethyl acetate (90 mL). This was extracted with 1 M hydrochloric acid (3×30 mL) and the combined extracts taken to pH8 with solid sodium bicarbonate. This was extracted with dichloromethane (3×30 mL) and the combined extracts dried (MgSO$_4$) and concentrated in vacuo. The residue was purified by flash chromatography on silica gel (Merck 9385) eluting with 200:8:1 dichloromethane:ethanol:ammonia to afford a gum (0.466 g). This was dissolved in dichloromethane (20 mL), treated with 1M hydrogen chloride in ether (5 mL) and concentrated in vacuo. Recrystallisation from 7% water in isopropanol (75 mL) gave Example 6 as a white powder (0.298 g). M.p. 194–195° C.

$^1$H-NMR (CD$_3$OD, 57° C., 400MHz) δ 4.40 (t, 2H), 4.28 (bs, 2H), 3.88 (m, 1H), 3.83–3.71 (m, 3H), 3.59 (sextet, 1H), 3.36 (t, 1H), 3.23(s, 3H), 3.10 (s, 2H), 3.03–2.96 (m, 1H), 2.95–2.90 (m, 1H), 2.52 (quintet, 1H), 2.12 (quintet, 1H), 1.27 (d, 3H), 1.04 (s, 9H), 1.02 (d, 3H).

IR (KBr diffuse reflectance) 3479, 3415, 2966, 2608, 1738, 1661cm$^{-1}$

Mass spec MH$^+$ (found) 400.226259, MH$^+$ (expected) 400.227004 (1.9 ppm).

Tlc SiO$_2$ (100:8:1 dichloromethane:ethanol:ammonia): R$_f$ 0.56

Combustion analysis: Found: C, 50:80; H,7.76; N, 9.37; S,6.97% C$_{19}$H$_{33}$N$_3$O$_4$S0.8H$_2$O HCl reuires C, 50.67; H, 7.97; N, 9.33; S, 7.12% HPLC (Inertsil ODS2-IK5, 40° C., 215 nm, 1 mL/min, solvent A H$_2$O+0.1% H$_3$PO$_4$, solvent B 95% MeCN/H$_2$O+0.1% H$_3$PO$_4$, gradient 0% B for 2 min, to 100% B in 40 min, 100% B for 10 min) retention time 14.247 min. (Chiralcel OD-H, 25° C., 215 nm, 1 mL/min, isocratic 60% EtOH in heptane) retention time 7.796 min.

Biological Data

1. The compounds of Examples 1 to 6 were tested in the in vitro elastase test described earlier in the description. The IC$_{50}$ values are given in the table below.

| Example | IC$_{50}$ (nM) |
| --- | --- |
| 1 | 194 |
| 2 | 229 |
| 3 | 83 |
| 4 | 210 |
| 5 | 93 |
| 6 | 37 |

2. The compound of Example 3 was tested in the in vivo hamster IL-8 test described earlier in the description and showed a duration of action of at least 6 hours at a dose of less than 10 mg/kg.

3. The compounds of Examples 1 to 6 were tested in the human whole blood elastase inhibition assay described earlier in the description. The IC$_{50}$ values are given in the table below.

| Example | IC$_{50}$ (µM) |
| --- | --- |
| 1 | 5.4 |
| 2 | 0.81 |
| 3 | 0.46 |
| 4 | 1.2 |
| 5 | 1.7 |
| 6 | 0.19 |

What is claimed is:
1. A compound of formula (I)

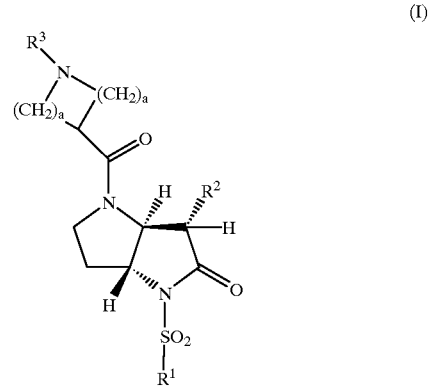

(relative stereochemistry indicated)
wherein:
R$^1$ represents C$_{1-4}$ alkyl;
R$^2$ represents C$_{2-4}$ alkyl or C$_{2-4}$alkenyl;
a represents 1 or 2;
R$^3$ represents C$_{1-8}$ alkyl or (CH$_2$)$_n$Ar;
n represents 1 or 2;
Ar represents optionally substituted phenyl;
and salts and solvates thereof.

2. A compound of formula (I) according to claim 1 wherein R$^2$ represents isopropyl or propyl.

3. A compound of formula (I) according to claim 2 wherein R$^2$ represents isopropyl.

4. A compound of formula (I) according to claim 1 wherein a represents 1.

5. A compound of formula (I) according to claim 1 wherein R$^1$ represents methyl or ethyl.

6. A compound of formula (I) according to claim 5 wherein R$^1$ represents ethyl.

7. A compound of formula (I) according to claim 1 wherein R$^3$ represents C$_{1-8}$ alkyl or —CH$_2$Ar.

8. A compound of formula (I) according to claim 7 wherein R$^3$ represents a C$_{1-8}$ alkyl group selected from n-butyl, cyclopropyl and t-butyl or a —CH$_2$Ar group wherein Ar is selected from phenyl and phenyl substituted by one or more halogen groups.

9. A compound of formula (I) according to claim 1 which is rel-(3R,3aR,6aS)-4-(1-Cyclopropylmethyl-azetidine-3-carbonyl)-3-isopropyl-1-methanesulfonyl-hexahydro-pyrrolo[3,2-b]pyrrol-2-one;

rel-(3R,3aR,6aS)-(1-Benzyl-azetidine-3-carbonyl)-3-isopropyl-1-methanesulfonyl-hexahydro-pyrrolo[3,2-b]pyrrol-2-one;

rel-(3R,3aR,6aS)-4-[1-(2,6-Dichloro-benzyl)-azetidine-3-carbonyl]-3-4-isopropyl-1-methanesulfonyl-hexahydro-pyrrolo[3,2-b]pyrrol-2-one;

rel-(3R,3aR,6aS)-4-(1-Butyl-azetidine-3-carbonyl)-3-isopropyl-1-methanesulfonyl-hexahydro-pyrrolo[3,2-b]pyrrol-2-one;

or a salt or solvate of any one thereof.

10. A compound of formula (I) according to claim 1 which is rel-(3R,3aR,6aS)-4-[1-(2,2-Dimethyl-propyl)-azetidine-3carbonyl]-3-isopropyl-1-methanesulfonyl-hexahydropyrrolo[3,2-b]pyrrol-2-one or a salt or solvate thereof.

11. A compound of formula (I) according to claim 1 which is rel-(3R,3aR,6aS)-4-[1-(2,2-Dimethyl-propyl)azetidine-3-carbonyl]-3-isopropyl-1-methanesulfonyl-hexahydropyrrolo[3,2-b]pyrrol-2-one hydrochloride.

12. A purified single enantiomer of a compound of formula (I) according to claim 1 having absolute stereochemistry as illustrated in formula (I).

13. A compound of formula (I) according to claim 1 which is (3S,3aS,6aR)-4-[1-(2,2-Dimethyl-propyl)-azetidine-3-carbonyl]3-isopropyl-1-methanesulfonyl-hexahydropyrrolo[3,2-b]pyrrol-2-one or a salt or solvate thereof.

14. A compound of formula (I) according to claim 1 which is (3S,3aS,6aR)-4-[1-(2,2-Dimethyl-propyl)-azetidine-3carbonyl]-3-isopropyl-1-methanesulfonyl-hexahydropyrrolo[3,2-b]pyrrol-2-one hydrochloride.

15. A compound of formula (I) according to claim 1 for use as a pharmaceutical.

16. A pharmaceutical composition comprising a compound formula (I) according to claim 1 in admixture with one or more physiologically acceptable diluents or carriers.

17. A method of treatment of chronic bronchitis or chronic obstructive pulmonary disease in a human or animal subject which comprises administering to said human or animal subject an effective amount of a compound of formula (I) according to claim 1.

18. A method of treatment of asthma in a human or animal subject which comprises administering to said human or animal subject an effective amount of a compound of formula (I) according to claim 1.

19. A compound of formula (III)

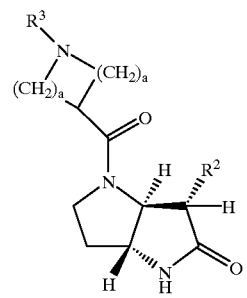

(III)

(relative stereochemistry indicated)
wherein $R^2$, $R^3$ and a are as defined in claim 1
or a protected derivative thereof.

20. A compound of formula (V)
(relative stereochemistry indicated)
wherein $R^1$, $R^2$ and $R^3$ are as defined in claim 1 and $X_a$ represents sulphur or SO.

21. A compound of formula (VI)

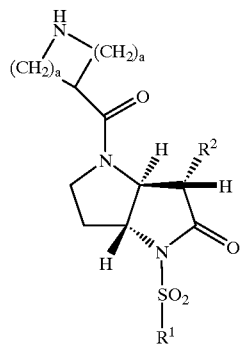

(VI)

(relative stereochemistry indicated)
wherein $R^1$ and $R^2$ are as defined in claim 1.

* * * * *